United States Patent
Zhou (10) Patent No.: US 10,405,706 B2
(45) Date of Patent: Sep. 10, 2019

(54) SMART TOILET HAVING FUNCTION OF HUMAN BLOOD OXYGEN DETECTION

(71) Applicant: Zhongshan Anbo Health Technology Co., Ltd., Zhongshan (CN)

(72) Inventor: Wenhui Zhou, Zhongshan (CN)

(73) Assignee: ZHONGSHAN ANBO HEALTH TECHNOLOGY CO., LTD., Zhongshan (CN)

( * ) Notice: Subject to any disclaimer, the term of this patent is extended or adjusted under 35 U.S.C. 154(b) by 0 days.

(21) Appl. No.: 15/916,285

(22) Filed: Mar. 9, 2018

(65) Prior Publication Data

US 2018/0271339 A1   Sep. 27, 2018

(30) Foreign Application Priority Data

Mar. 24, 2017   (CN) .......................... 2017 1 0182425

(51) Int. Cl.
| | |
|---|---|
| *A47K 13/24* | (2006.01) |
| *A61B 5/1455* | (2006.01) |
| *A61B 5/00* | (2006.01) |
| *A47K 17/02* | (2006.01) |

(52) U.S. Cl.
CPC ............ *A47K 13/24* (2013.01); *A61B 5/1455* (2013.01); *A61B 5/14551* (2013.01); *A61B 5/6891* (2013.01); *A47K 17/02* (2013.01)

(58) Field of Classification Search
CPC .............................. A47K 13/24; A61B 5/1455
See application file for complete search history.

(56) References Cited

U.S. PATENT DOCUMENTS

| | | | | |
|---|---|---|---|---|
| 6,064,898 A | * | 5/2000 | Aldrich | A61B 5/14532 600/316 |
| 9,828,755 B1 | * | 11/2017 | Clements | E03D 9/08 |
| 2018/0084959 A1 | * | 3/2018 | Hall | A47K 13/24 |

\* cited by examiner

*Primary Examiner* — Janie M Loeppke
(74) *Attorney, Agent, or Firm* — Gokalp Bayramoglu (57) ABSTRACT

A smart toilet having a function of human blood oxygen detection is provided. The smart toilet includes a toilet base and a machine body connected to the toilet base. The machine body is provided with a controller and the following modules which are electrically connected to controller respectively, i.e., human blood oxygen detection module, display or voice prompt module, and power supply module which is used to supply power. After processing, the controller obtains the human blood oxygen saturation value based on the electrical signal transferred from the human blood oxygen detection module. Also, the controller controls the display or voice prompt module to output the human blood oxygen saturation value. The present invention combines the toilet with the human blood oxygen detection, such that it is easy for the user to know about his/her blood oxygen condition in real time.

4 Claims, 4 Drawing Sheets

SMART TOILET HAVING FUNCTION OF HUMAN BLOOD OXYGEN DETECTION

CROSS REFERENCE TO RELATED APPLICATIONS

This application is based upon and claims priority to Chinese Patent Application No. 201710182425.2, filed on Mar. 24, 2017, the entire content of which is incorporated herein by reference.

TECHNICAL FIELD

The present invention relates to a toilet, particularly to a smart toilet having a function of human blood oxygen detection.

BACKGROUND OF THE INVENTION

The main functions of existing smart toilets include heating-up of the toilet seat, washing with warm water, drying with warm air, and deodorization. However, the general functions are limited, and the usage is invariant. It is hard to get a breakthrough in terms of functions. In recent years, with the increasing requirements of people for the quality of life, the demand for quality health is getting higher and higher. It is a trend that the personal health care functions are combined into the smart toilets. However, currently, some smart toilets cannot satisfy the requirements of people to understand their health condition. Meanwhile, people with vascular diseases, people with diseases of the respiratory system, senior people, and people who work for long hours often have a low concentration of blood oxygen due to insufficient oxygen intake. This condition may damage the human organs and even endanger the life in a serious case. How to quickly and conveniently detect blood oxygen for people has become a considerable health subject.

SUMMARY OF THE INVENTION

In order to address the deficiencies of the prior art, the present invention provides a smart toilet having a function of human blood oxygen detection. While the user is using the toilet, the human blood oxygen saturation value can be detected quickly and conveniently, such that the requirements of people who want to know their health conditions can be satisfied.

The present invention uses the following technical solutions:

A smart toilet having a function of human blood oxygen detection is provided. The smart toilet includes toilet base 2, wherein the smart toilet further includes machine body 1 which is connected to the toilet base. The machine body 1 is provided with controller 3 and the following modules which are electrically connected to controller 3 respectively, i.e., human blood oxygen detection module 4, display or voice prompt module 5, and power supply module 30 which is used to supply power. The human blood oxygen detection module 4 includes two or more LEDs 40 and power supply control circuit 41. LEDs 40 release light beams with and is used to intermittently supply power to LEDs. The human blood oxygen detection module 4 further includes photoelectric sensor 42 which is electrically connected to controller 3. The photoelectric sensor 42 receives the optical signals going through the finger of the human body and converts the optical signals into an electrical signal to transfer to controller 3. After processing, the controller 3 obtains human blood oxygen saturation value based on the received electrical signal and controls display or voice prompt module 5 to output the human blood oxygen saturation value.

The machine body 1 is further provided with key input module 6 which is electrically connected to controller 3 and is used to send the operating information of the user back to the controller 3.

The machine body 1 includes main body 10, and toilet seat 12 pivotally connected to main body 10, wherein after being rotated, toilet seat 12 covers the toilet base 2.

The machine body 1 includes main body 10 and arm 11 which is provided on main body 10. The arm 11 is provided with finger hole 111 which is used to receive an inserted finger of a person. LEDs 40 and photoelectric sensor 42 are provided inside the finger hole 111. LEDs 40 are provided opposite to photoelectric sensor 42 such that after the finger is inserted into the finger hole, the finger is positioned between the LEDs and the photoelectric sensor.

There are two LEDs 40 that release optical signals with different wavelengths, i.e., the first LED and the second LED respectively.

The smart toilet further includes human body sensing module 7 which is electrically connected to the controller 3 and is used to sense whether the human body has sat down.

The human body sensing module 7 includes a capacitive sensor, a pressure sensor, or an inductive electrode plate which is electrically connected to controller 3 and is used to sense whether the user has sat down. The capacitive sensor, the pressure sensor, or the inductive electrode plate is provided on the toilet base 2 or machine body 1.

The smart toilet further includes the toilet seat temperature control module 8 which is electrically connected to controller 3 and controls the temperature of the toilet seat. The toilet seat temperature control module 8 includes a temperature sensor and the toilet seat heating module which are provided on the toilet seat and are electrically connected to the controller respectively.

The smart toilet further includes user cleaning module 9 which is electrically connected to controller 3. The user cleaning module 9 includes water spray module 90 which provides cleaning water, water pressure control module 91 which controls the pressure of the outlet water of the cleaning water, water temperature control module 92 which controls the temperature of the outlet water of the cleaning water, fan module 94 which provides the drying air, and air temperature control module 93 which controls the temperature of the drying air. The water pressure control module 91, water temperature control module 92, and air temperature control module 93 are electrically connected to controller 3.

The water spray module 90 includes a nozzle for outlet water and a water pipe connecting the nozzle to an external water source. The water temperature control module 92 includes the temperature sensor and the cleaning water heating module which are provided on the water pipe and are electrically connected to controller 3 respectively. The water pressure control module 91 includes a proportional valve which is provided between the nozzle and the water pipe, and is electrically connected to the controller. The air temperature control module 93 includes a temperature sensor and a drying air heating module which are electrically connected to the controller respectively.

The smart toilet further includes communication module 31 which is electrically connected to the controller. The communication module 31 communicates with a smart device. The human blood oxygen saturation value is transferred through the communication module to the smart device and is displayed thereon.

A control method of a smart toilet having a function of human blood oxygen detection is provided, wherein the method includes the following steps:

A: Power-on and initialization: an initial state of each connected module is initialized through controller 3.

B: Execution of power-on self-checking: a fault detection is conducted by controller 3 on each module. If the self-checking is passed, the procedure proceeds to step C. Otherwise, an exception handling is performed, and exception information is displayed or reported through display or voice prompt module 5.

C: Entering the main cycle, controller 3 detects whether someone has sat down through human body sensing module 7. If someone has sat down, controller 3 starts human blood oxygen detection module 4 to conduct the blood oxygen detection. Human blood oxygen detection module 4 obtains an electrical signal which is related to human blood oxygen saturation value, and transfer the electrical signal to the controller. After processing, the controller obtains a human blood oxygen saturation value based on obtained electrical signal and controls display or voice prompt module 5 or communication module 31 communicating with the smart device to output the human blood oxygen saturation value. Then, the procedure proceeds to step D. If nobody has sat down, controller 3 controls human blood oxygen detection module 4 to enter dormancy, and the procedure proceeds to step D.

D: Controller 3 detects whether there is input at key input module 6. If there is no input, the procedure returns to step C. If there is an input, the procedure proceeds to step E.

E: Controller 3 performs corresponding operations based on the input at key input module 6: setting the temperature of the outlet water of the cleaning water, the water pressure of the outlet water of the cleaning water, and the temperature of the drying air; starting user cleaning module 9 to provide cleaning water or drying air.

The smart toilet includes toilet base 2. The smart toilet further includes machine body 1 which is connected to the toilet base. The machine body 1 is provided with controller 3 and following modules which are electrically connected to controller 3 respectively, i.e., human blood oxygen detection module 4, display or voice prompt module 5, and power supply module 30 which is used to provide power. The human blood oxygen detection module 4 includes two or more LEDs 40 which release light beams with different wavelengths and power supply control circuit 41 which is controlled by controller 3 and is used to intermittently supply power to LEDs. The human blood oxygen detection module 4 further includes photoelectric sensor 42 which is electrically connected to controller 3. The photoelectric sensor 42 receives the optical signals of the LEDs going through the finger of the human body and converts the optical signals into an electrical signal to transfer to controller 3. After processing, the controller 3 obtains a human blood oxygen saturation value based on the received electrical signal and controls display or voice prompt module 5 to output the human blood oxygen saturation value.

The smart toilet further includes human body sensing module 7 which is electrically connected to the controller 3 and is used to sense whether the human body has sat down.

The smart toilet further includes user cleaning module 9 which is electrically connected to controller 3. The user cleaning module 9 includes water spray module 90 which provides cleaning water, water pressure control module 91 which controls the pressure of the outlet water of the cleaning water, water temperature control module 92 which controls the temperature of the outlet water of the cleaning water, fan module 94 which provides the drying air, and air temperature control module 93 which controls the temperature of the drying air. The water pressure control module 91, water temperature control module 92, and air temperature control module 93 are electrically connected to controller 3.

The machine body 1 includes main body 10, and toilet seat 12 pivotally connected to main body 10, wherein toilet seat 12, after being rotated, covers the toilet base 2. The smart toilet further includes the toilet seat temperature control module 8 which is electrically connected to controller 3 and controls the temperature of the toilet seat. The toilet seat temperature control module 8 includes a temperature sensor and a toilet seat heating module which are provided on the toilet seat and are electrically connected to the controller respectively. Step E further includes performing corresponding operations by controller 3 based on the input at key input module 6, i.e., setting the temperature of the toilet seat, starting toilet seat temperature control module 8 to adjust the temperature of the toilet seat.

Step E further includes performing corresponding operations by controller 3 based on the input at key input module 6. More specifically, controller 3 starts human blood oxygen detection module 4 to conduct the blood oxygen detection. Human blood oxygen detection module 4 obtains an electrical signal which is related to human blood oxygen saturation value and transfers the electrical signal to the controller. After processing, the controller obtains human blood oxygen saturation value based on the obtained electrical signal and controls display or voice prompt module 5 or communication module (31) communicating with the smart device to output human blood oxygen saturation value.

The human body sensing module 7 includes a capacitive sensor, a pressure sensor, or an inductive electrode plate which is electrically connected to controller 3 and is used to sense whether the user has sat down. The capacitive sensor, the pressure sensor, or the inductive electrode plate is provided on the toilet base 2 or machine body 1.

Compared with the prior art, the smart toilet having a function of human blood oxygen detection of the present invention has the following advantages:

The smart toilet includes toilet base. The smart toilet further includes a machine body which is connected to the toilet base. The machine body is provided with controller and the following modules which are electrically connected to controller respectively, i.e., human blood oxygen detection module, display or voice prompt module, and power supply module which is used to supply power. The human blood oxygen detection module detects the optical signals which are emitted by the LEDs and go through a finger of the human body. Also, the human blood oxygen detection module converts the optical signals into electrical signals, which are transferred to the controller. After processing, the controller obtains the human blood oxygen saturation value based on the received electrical signals. Also, the controller controls the display or voice prompt module to output the human blood oxygen saturation value. The present invention combines the toilet with the detection of human blood oxygen, such that it is easy for the user to know about his/her blood oxygen condition in real time while the user is using the toilet. Thus, the present invention has positive effects on preventing diseases of low blood oxygen and has advantages of convenience, intelligence, and simple operations.

2. The human blood oxygen detection module includes LEDs, a photoelectric sensor, and a power supply control circuit which supplies power to LEDs. The human blood oxygen detection module has advantages of a simple structure and low cost.

3. As a further improvement of the present invention, there are two LEDs which release optical signals with different wavelengths, i.e., the first LED and the second LED respectively. The machine body is provided with an arm. The arm is provided with a finger hole which is used to receive an inserted finger of a person. The LEDs and the photoelectric sensor are provided inside the finger hole. LEDs are provided opposite to the photoelectric sensor such that after the finger is inserted into the finger hole, the finger is positioned between LEDs and the photoelectric sensor. When the user is sitting on the toilet of the present invention and is using the toilet, the user only needs to insert his/her finger into the finger hole in the arm to detect the blood oxygen value. Thus, the detection of blood oxygen is more convenient.

4. As a further improvement of the present invention, the present invention further includes a human body sensing module which is electrically connected to the controller and is used to sense whether the human body has sat down. When the user is sitting on the toilet of the present invention, the controller learns that the user has sat down on the toilet of the present invention through the human body sensing module. Thus, the human blood oxygen detection module can be started to acquire and output human blood oxygen data. The configuration of human body sensing module can facilitate the intellectualized control of the present invention, making the blood oxygen detection more convenient. When the user leaves, modules which are not in use can automatically enter dormancy, such that the energy can be saved.

DETAILED DESCRIPTION OF THE INVENTION

Hereinafter, embodiments of the present invention are described in detail with reference to FIG. 1 to FIG. 5.

Figure 1:
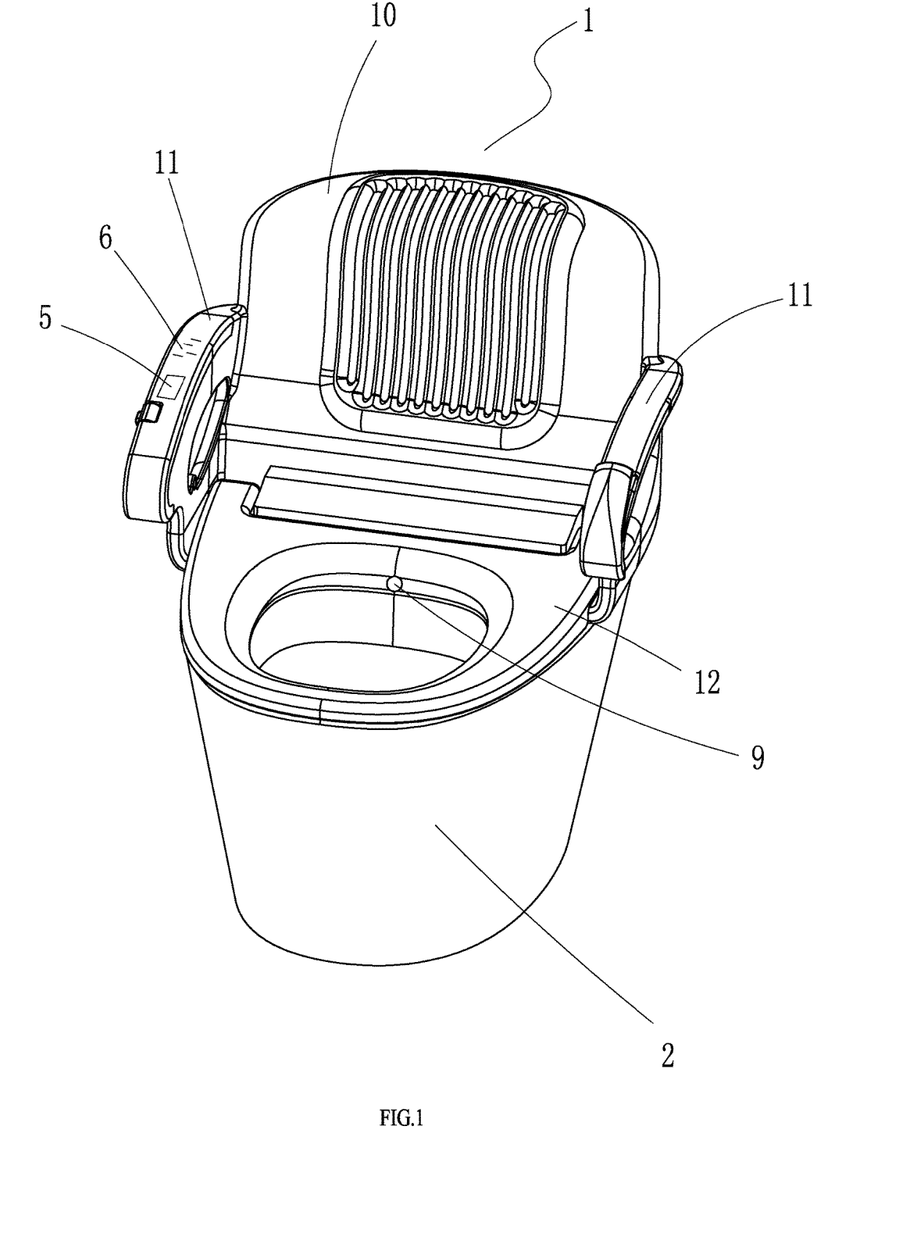
FIG. 1 is a three-dimensional schematic diagram of the present invention.
Figure 3:
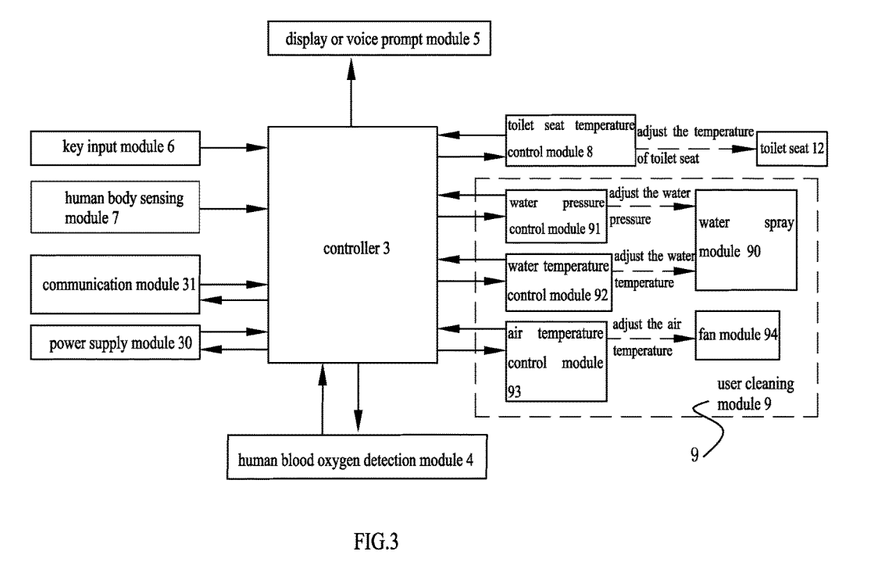
FIG. 3 is a diagram of the constitution of the system of the present invention.
Figure 4:
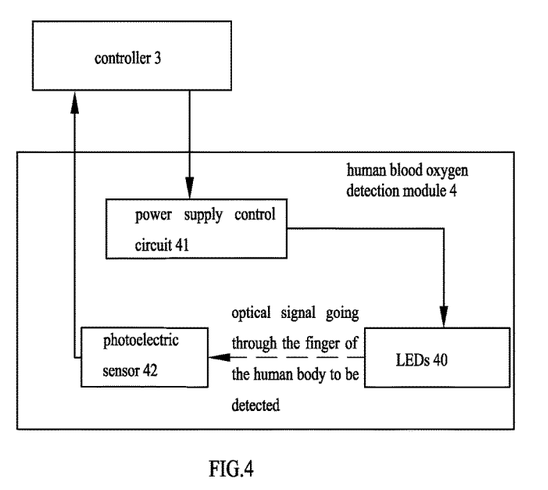
FIG. 4 is a diagram of the constitution of human blood oxygen detection module of the present invention.

A smart toilet having a function of human blood oxygen detection is provided. The smart toilet includes toilet base 2, wherein the smart toilet further includes machine body 1 which is connected to the toilet base. The machine body 1 is provided with controller 3 and the following modules which are electrically connected to controller 3 respectively, i.e., human blood oxygen detection module 4, display or voice prompt module 5, and power supply module 30 which is used to supply power. The human blood oxygen detection module 4 includes two or more LEDs 40 and power supply control circuit 41. The two or more LEDs 40 release light beams with different wavelengths. Power supply control circuit 41 is controlled by controller 3 and is used to intermittently supply power to the LEDs. The human blood oxygen detection module 4 further includes photoelectric sensor 42 which is electrically connected to controller 3. The photoelectric sensor 42 receives optical signals of the LEDs going through the finger of the human body and converts the optical signals into electrical signals, which are transferred to controller 3. After processing, the controller 3 obtains human blood oxygen saturation value based on the received electrical signals and controls display or voice prompt module 5 to output the human blood oxygen saturation value. The electrical signals refer to current or voltage signals. The photoelectric sensor 42 refers to a photosensitive element or a photoelectric detector which can convert the optical signals into the electrical signals.

The blood oxygen content is usually represented by a percentage of oxyhemoglobin with respect to total hemoglobin in the blood and is named as blood oxygen saturation. A measurement of blood oxygen saturation can be divided into two categories, i.e., an invasive measurement and a non-invasive measurement. The invasive measurement is to conduct the blood oxygen analysis after sampling the blood. However, the human blood oxygen detection module of the present invention uses the non-invasive measurement with spectrophotometry measuring principle. Since different ingredients in the blood have different absorbances of the same light, the contents of different ingredients in the blood can be calculated by detecting the degrees of attenuation of different lights going through the blood.

When a person is sitting on the smart toilet of the present invention, the finger to be tested is put between the LEDs and photoelectric sensor. LEDs respectively release light beams with different wavelengths. In order to avoid interference between lights, the power supply control circuit intermittently supply power to each LED. That is, only one LED emits a light beam at one time. LEDs are alternately powered, which is achieved by the power supply control circuit that is electrically connected to the controller. After light beams emitted from LEDs go through the human finger, a part of the lights will be absorbed. Lights which are not absorbed by the finger can be detected by the photoelectric sensor. Since absorbance of oxygen-containing hemoglobin is significantly different from the absorbance of oxygen-free hemoglobin with respect to light beams with different wavelengths, particularly for light beams with wavelengths of 660 nm, 905 nm, 910 nm, and 940 nm. With such character, the photoelectric sensor respectively receives optical signals after two or more light beams with different wavelengths go through the finger. Meanwhile, the optical signals are converted into electrical signals, which are transferred to the controller. The controller performs operations such as filtering, amplifying, analog-to-digital conversion, and so on, on the received electrical signals. Also, the controller calculates the blood oxygen saturation value based on the signals. The blood oxygen saturation refers to the percentage of the volume of the combined oxygen with respect to the total combinable oxygen volume in the total blood volume. The human blood oxygen saturation value will be output through the display or voice prompt module.

In order to facilitate the user to control the present invention, the machine body 1 is further provided with key input module 6 which is electrically connected to controller 3 and is used to send the operating information of the user back to the controller 3.

In order to facilitate replacements, cleaning, and sitting-down of the user, the machine body 1 includes main body 10, toilet seat 12 which is pivotally connected to main body 10, wherein toilet seat 12, after being rotated, covers toilet base 2. The main body 10 can also be used as the backrest, such that the user feels comfortable while sitting on toilet base 2.

Figure 2:
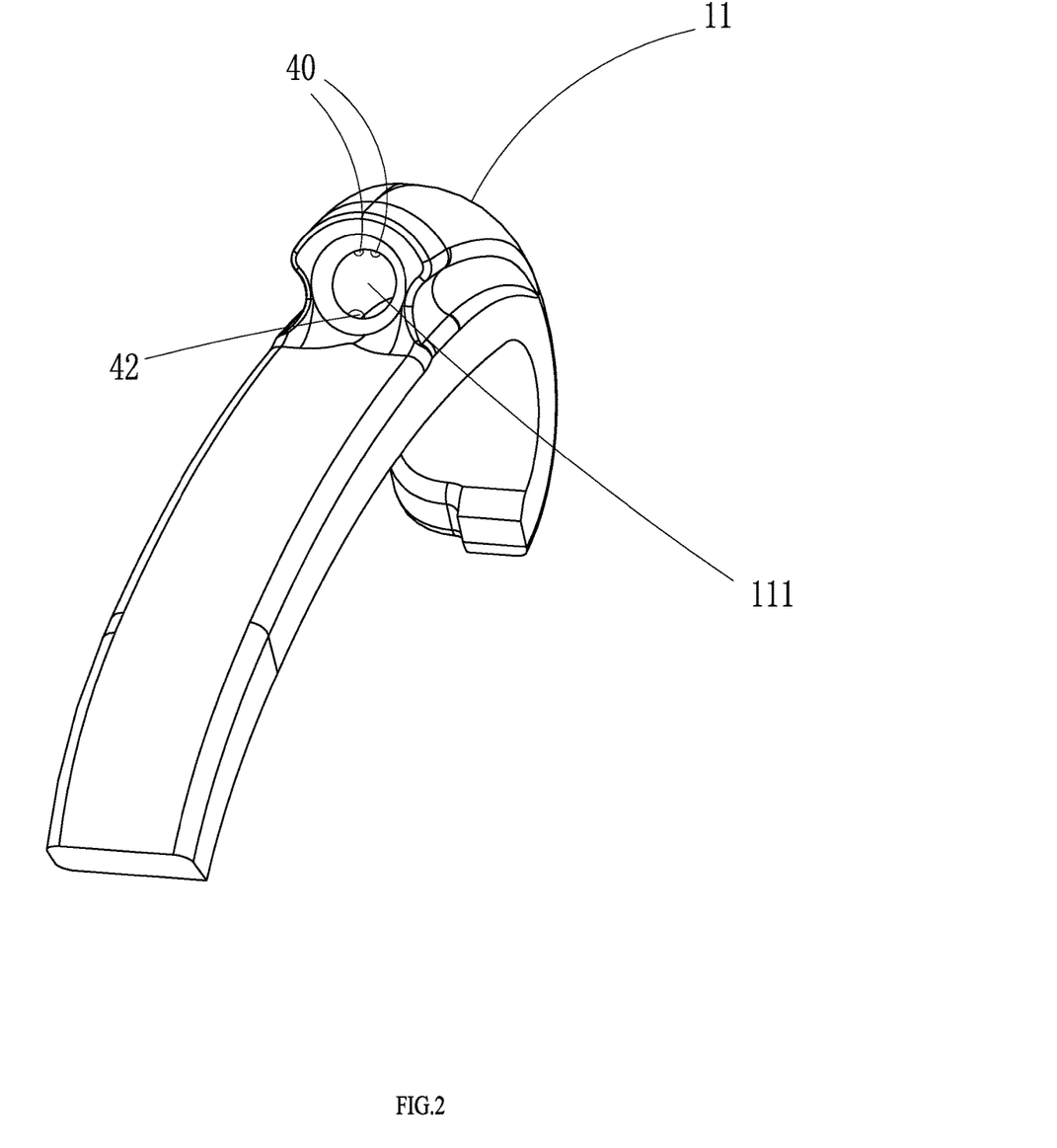
FIG. 2 is a schematic diagram of the structure of the arm of the present invention.

The machine body 1 includes arm 11 which is provided on main body 10. The arm 11 is provided with finger hole 111 which is used to receive an inserted finger of a person. The LEDs 40 and photoelectric sensor 42 are provided inside the finger hole 111. The LEDs 40 are provided opposite to photoelectric sensor 42 such that after the finger is inserted into the finger hole, the finger is positioned between LEDs and the photoelectric sensor. The LEDs 40 and photoelectric sensor 42 are provided inside the finger hole in the arm on the machine body. After the user sits down on the toilet seat on the toilet base or the machine body of the present invention, the user can conveniently and naturally put his/her finger into the finger hole in the arm. Thus, the operations of blood oxygen detection are convenient and simple. Additionally, in order to facilitate the operations of the present invention, the display or voice prompt module 5 and key input module 6 can be provided on arm 11.

Preferably, there are two LEDs 40 which release optical signals with different wavelengths, i.e., the first LED and the second LED respectively.

In order to facilitate the intellectualized control, the smart toilet further includes human body sensing module 7 which is electrically connected to the controller 3 and is used to sense whether the human body has sat down. The term "sit down" means that the user sits down on the toilet base or the toilet seat.

The preferable design of the human body sensing module 7 is as follows. The human body sensing module 7 includes a capacitive sensor, a pressure sensor, or an inductive electrode plate which is electrically connected to controller 3 and is used to sense whether the user has sat down. The capacitive sensor, the pressure sensor, or the inductive electrode plate is provided on the toilet base 2 or machine body 1. After the person sits down, the person directly or indirectly contacts the capacitive sensor, the pressure sensor, or the inductive electrode plate, causing the capacitance of the capacitive sensor to change, making the pressure sensor generate the piezoelectric effect, or leading to the change of current or the voltage of the circuit connected to the sensor or the inductive electrode plate. The electrical parameters, the electrical signal, or changes in the current or the voltage can be identified by the controller. Therefore, the controller can determine whether the user has sat down.

The above human body sensing module 7 uses the capacitive sensor, the pressure sensor, or the inductive electrode plate to sense whether the human body has sat down. Certainly, the human body sensing module 7 can also use the following manner to sense whether the human body has sat down. An infrared detecting sensor is used to detect the infrared rays generated by the human body to sense sitting-down of the human body. The bioelectricity of human body or the property of human body conduction is used to detect whether the human body has sat down. The above scenarios all belong to the category of human body sensing detecting module and should fall within the protective scope of the present invention.

In order to enrich the functions, the smart toilet further includes the toilet seat temperature control module 8 which is electrically connected to controller 3 and controls the temperature of the toilet seat. The toilet seat temperature control module 8 includes a temperature sensor and a toilet seat heating module which are provided on the toilet seat and are electrically connected to the controller respectively. The toilet seat heating module can include an electrical heating tube, an electrical heating wire, or an electromagnetic heating group, and further includes some necessary power supplies and control circuits. The user can conveniently adjust the temperature of the toilet seat through the toilet seat temperature control module 8, which is helpful to improve the experience of the user of the present invention.

The user can set the temperature of the toilet seat through the controller and the key input module. When the temperature sensor detects that the temperature of the toilet seat does not reach the set temperature, the controller controls the toilet seat heating module to heat up the toilet seat. When the temperature sensor detects that the temperature of the toilet seat is over the set temperature, the controller controls the toilet seat heating module to stop heating. The temperature of the toilet seat can be maintained at the set temperature through the above operations.

In order to enrich the functions, the smart toilet further includes user cleaning module 9 which is electrically connected to controller 3. The user cleaning module 9 includes water spray module 90 which provides cleaning water, water pressure control module 91 which controls the pressure of the outlet water of the cleaning water, water temperature control module 92 which controls the temperature of the outlet water of the cleaning water, fan module 94 which provides the drying air, and air temperature control module 93 which controls the temperature of the drying air. The water pressure control module 91, water temperature control module 92, and air temperature control module 93 are electrically connected to controller 3. After the user uses the toilet, the user informs the controller to start the user cleaning module through the key input module. The user cleaning module cleans and dries the user based on the water temperature of the cleaning water, the water pressure, and the temperature of the drying air as set by the user. The cleaning includes hip washing and female washing. The cleaning water is provided by water spray module. The water spray module is controlled by water temperature control module 92 and water pressure control module 91. The user can set the water pressure and the water temperature of the cleaning water through the controller. The drying air is provided by fan module. The fan module is controlled by air temperature control module. The user can set the air temperature of the drying air through the controller.

The water spray module 90 includes a nozzle for outlet water and a water pipe connecting the nozzle to an external water source. The water temperature control module 92 includes a temperature sensor and a cleaning water heating module which are provided on the water pipe and are electrically connected to controller 3 respectively. The water pressure control module 91 includes a proportional valve which is provided between the nozzle and the water pipe and is electrically connected to the controller. The air temperature control module includes a temperature sensor and a drying air heating module which are electrically connected to the controller respectively. The user can set the water temperature and the water pressure of the outlet water of the cleaning water through the controller and the key input module. The controller heats up the cleaning water in the water pipe based on the set water temperature of the cleaning water. The temperature sensor senses the temperature of the cleaning water in the water pipe. If the temperature is lower than the set temperature, the cleaning water heating module is started to heat up the cleaning water. If the temperature is higher than the set temperature, the cleaning water heating module is turned off. As such, the temperature of the outlet water of the cleaning water is kept constant. The proportional valve is provided between the nozzle and the water pipe. The proportional valve is electrically connected to the controller and is controlled by the controller. The controller adjusts an opening degree of the proportional valve based on the set water pressure of the outlet water of the cleaning water, so as to adjust the water pressure of the outlet water of the cleaning water. In addition, the user can also set the temperature of the drying air through the controller. The air temperature control module includes the temperature sensor and the drying air heating module which are electrically connected to the controller respectively. When the temperature of the drying air is lower than the set temperature of drying air, the drying air heating module is started, so as to heat up the drying air. When the temperature of the drying air is higher than the set temperature, the heating of drying air is stopped. With the above method, the air temperature control module keeps the temperature of the drying air at the set temperature. The drying air heating module and cleaning water heating module can be a heating wire, a heating rod, an electromagnetic heating group, along with corresponding power supply circuit and control circuit.

The smart toilet further includes communication module 31 which is electrically connected to the controller. The communication module 31 communicates with a smart device. The human blood oxygen saturation value is transferred through the communication module to the smart device and is displayed thereon. The smart device can be a cellphone, a computer, etc. The communication module communicates with the smart device. The communicating method can be WIFI, infrared communication, NFC near field communication, etc. The smart device, such as the cellphone, can display the human blood oxygen saturation value with an APP. Certainly, the smart device can also control the toilet of the present invention through the communication module.

In order to facilitate controlling the present invention, a control method is provided as below.

Figure 5:
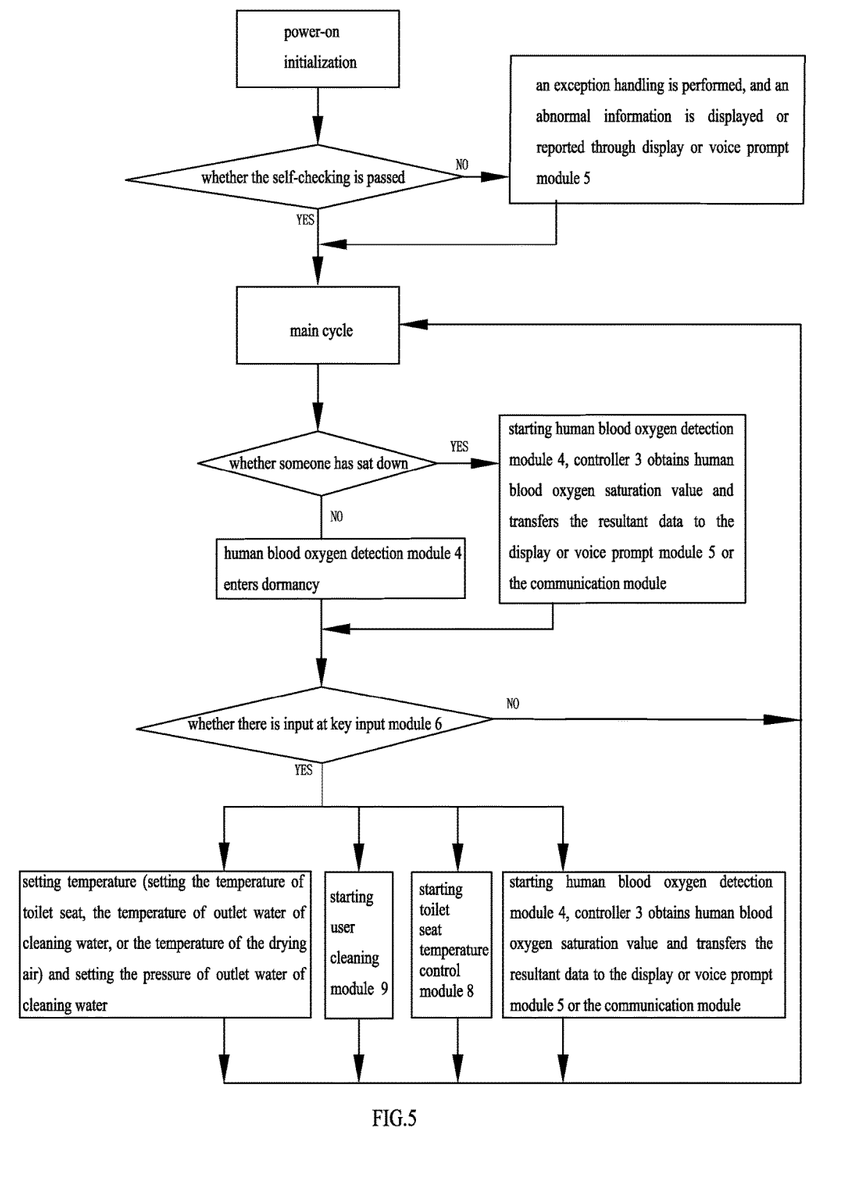
FIG. 5 is a flowchart of a control method of the present invention.

A control method of a smart toilet having a function of human blood oxygen detection, wherein the method includes the following steps:

A: Power-on and initialization: an initial state of each connected module is initialized through controller 3.

B: Execution of power-on self-checking: a fault detection is conducted by controller 3 on each module. If the self-checking is passed, the procedure proceeds to step C. Otherwise, exception handling is performed, and exception information is displayed or reported on display or voice prompt module 5. The fault detection includes detecting whether there is short circuit, disconnection, or current/voltage overload in the circuit of each module and the controller circuit.

C: Entering the main cycle, controller 3 detects whether someone has sat down through human body sensing module 7. If someone has sat down, controller 3 starts human blood oxygen detection module 4 to conduct the blood oxygen detection. Human blood oxygen detection module 4 obtains electrical signals which are related to human blood oxygen saturation value and are transferred to the controller. After processing, the controller obtains human blood oxygen saturation value based on the obtained electrical signals and controls display or voice prompt module 5 or communication module 31 communicating with the smart device to output human blood oxygen saturation value. Then, the procedure proceeds to step D. If nobody has sat down, controller 3 controls human blood oxygen detection module 4 to enter dormancy, and the procedure proceeds to step D. The dormancy can be achieved by the controller which cuts off the power supply of the human blood oxygen detection module. More specifically, the power supply to LEDs is stopped. The step of starting the human blood oxygen detection module refers to supplying power to the human blood oxygen detection module, more particularly, supplying power to the LEDs. Certainly, the user needs to put his/her finger between LEDs and the photoelectric sensor in human blood oxygen detection module 4 such that the controller can obtain meaningful electrical signals and obtain the human blood oxygen value after processing.

D: Controller 3 detects whether there is an input at key input module 6. If there is no input, the procedure returns to the step C. If there is an input, the procedure proceeds to step E.

E: Controller 3 performs corresponding operations based on the input at key input module 6: setting the temperature of the outlet water of the cleaning water, the water pressure of the outlet water of the cleaning water, and the temperature of the drying air; starting user cleaning module 9 to provide cleaning water or drying air.

The smart toilet includes toilet base 2. The smart toilet further includes machine body 1 which is connected to the toilet base. The machine body 1 is provided with controller 3 and the following modules which are electrically connected to controller 3 respectively, i.e., human blood oxygen detection module 4, display or voice prompt module 5, power supply module 30 which is used to supply power. The human blood oxygen detection module 4 includes two or more LEDs 40 and power supply control circuit 41. The two or more LEDs 40 release light beams with different wavelengths. Power supply control circuit 41 is controlled by controller 3 and is used to intermittently supply power to the LEDs. The human blood oxygen detection module 4 further includes photoelectric sensor 42 which is electrically connected to controller 3. The photoelectric sensor 42 receives optical signals of the LEDs going through the finger of the human body and converts the optical signals into electrical signals, which are transferred to controller 3. After processing, the controller 3 obtains human blood oxygen saturation value based on the received electrical signals and controls display or voice prompt module 5 to output the human blood oxygen saturation value.

The smart toilet further includes human body sensing module 7 which is electrically connected to the controller 3 and is used to sense whether the human body has sat down.

The smart toilet further includes user cleaning module 9 which is electrically connected to controller 3. The user cleaning module 9 includes water spray module 90 which provides cleaning water, water pressure control module 91 which controls the pressure of the outlet water of the cleaning water, water temperature control module 92 which controls the temperature of the outlet water of the cleaning water, fan module 94 which provides the drying air, and air temperature control module 93 which controls the temperature of the drying air. The water pressure control module 91, water temperature control module 92, and air temperature control module 93 are electrically connected to controller 3.

The machine body 1 includes main body 10, toilet seat 12 which is pivotally connected to main body 10, wherein toilet seat 12, after being rotated, covers toilet base 2. The smart toilet further includes the toilet seat temperature control module 8 which is electrically connected to controller 3 and controls the temperature of the toilet seat. The toilet seat temperature control module 8 includes a temperature sensor and a toilet seat heating module which are provided on the toilet seat and are electrically connected to the controller respectively. Step E further includes performing corresponding operations based on the input at key input module 6 by controller 3: setting the temperature of the toilet seat, and starting the toilet seat temperature control module 8 to adjust the temperature of the toilet seat.

Step E further includes performing corresponding operations based on the input at key input module 6 by controller 3. Specifically, controller 3 starts human blood oxygen detection module 4 to conduct the blood oxygen detection. Human blood oxygen detection module 4 obtains electrical signals which are related to human blood oxygen saturation value and are transferred to the controller. After processing, the controller obtains human blood oxygen saturation value based on the obtained electrical signals and controls display or voice prompt module 5 or communication module 31 communicating with the smart device to output human blood oxygen saturation value.

The human body sensing module 7 includes a capacitive sensor, a pressure sensor, or an inductive electrode plate which is electrically connected to controller 3 and is used to sense whether the user has sat down. The capacitive sensor, the pressure sensor, or the inductive electrode plate is provided on the toilet base 2 or machine body 1. After the person sits down, the person directly or indirectly contacts the capacitive sensor, the pressure sensor, or the inductive electrode plate, causing the capacitance of the capacitive sensor to change, making the pressure sensor generate the piezoelectric effect, or leading to changes of the current or the voltage of the circuit connected to the sensor or inductive electrode plate. The electrical parameters, the electrical signals, or changes of the current or the voltage can be identified by the controller. Therefore, the controller can determine whether the user has sat down. The term "sit down" means that the user sits down on the toilet base or the toilet seat.

What is claimed is:

1. A control method of smart toilet having a function of human blood oxygen detection, comprising the following steps:
   A: initiating an initial state of each connected module through a controller;
   B: executing self-checking:
      conducting a fault detection on each module through the controller;
      if the self-checking is passed, proceeding to step C;
      otherwise, conducting an exception handling, displaying or reporting exception information through a display or voice prompt module;
   C: entering a main cycle,
      detecting whether someone has sat down by the controller with a human body sensing module;
      if someone has sat down, starting, by the controller, a human blood oxygen detection module to conduct blood oxygen detection;
      obtaining, by the human blood oxygen detection module, an electrical signal related to a human blood oxygen saturation value;
      transferring the electrical signal to the controller;
      after processing, obtaining, by the controller, the human blood oxygen saturation value based on the obtained electrical signal;
      controlling, by the controller, the display or voice prompt module or a communication module communicating to a smart device to output the human blood oxygen saturation value, and proceeding to step D;
      if nobody has sat down, controlling, by the controller, the human blood oxygen detection module to enter dormancy, and proceeding to step D;
   D: detecting, by the controller, whether there is an input at a key input module;
      if there is no input, returning to the step C;
      if there is the input, proceeding to step E;
   E: performing corresponding operations by the controller based on the input at the key input module:
      setting a temperature of outlet water of cleaning water;
      setting a water pressure of outlet water of cleaning water;
      setting a temperature of drying air;
      starting a user cleaning module to provide the cleaning water or the drying air;
   wherein
   the smart toilet includes a toilet base;
   the smart toilet further includes a machine body which is connected to the toilet base;
   the machine body is provided with the controller, the human blood oxygen detection module, the display or voice prompt module, and a power supply module;
   the power supply module is used to supply power;
   the human blood oxygen detection module, the display or voice prompt module, and the power supply module are electrically connected to the controller respectively;
   the human blood oxygen detection module includes two or more LEDs and a power supply control circuit;
   the two or more LEDs release light beams with different wavelengths;
   the power supply control circuit is controlled by the controller and supplies power to the LEDs intermittently;
   the human blood oxygen detection module further includes a photoelectric sensor;
   the photoelectric sensor is electrically connected to the controller; wherein the LEDs are provided opposite to the photoelectric sensor, such that after a finger is inserted into a finger hole, the finger is positioned between the LEDs and the photoelectric sensor;
   the photoelectric sensor receives optical signals of the LEDs after the optical signals go through the finger of a human body to be detected;
   the photoelectric sensor converts the optical signals into an electrical signal and transfers the electrical signal to the controller;
   after processing, the controller obtains a human blood oxygen saturation value based on the received electrical signal; and
   the controller controls the display or voice prompt module to output the human blood oxygen saturation value;
   the smart toilet further includes the human body sensing module;
   the human body sensing module is electrically connected to the controller and is used to sense whether the human body has sat down;
   the smart toilet further includes the user cleaning module;
   the user cleaning module is electrically connected to the controller;
   the user cleaning module includes a water spray module, a water pressure control module, a water temperature control module, a fan module, and an air temperature control module;
   the water spray module provides the cleaning water;
   the water pressure control module controls the water pressure of outlet water of the cleaning water;
   the water temperature control module controls the temperature of the outlet water of the cleaning water,
   the fan module provides the drying air;

the air temperature control module controls the temperature of the drying air; and the water pressure control module, the water temperature control module, the air temperature control module are electrically connected to the controller.

2. The control method of the smart toilet having the function of human blood oxygen detection of claim 1, wherein the machine body includes a main body, a turning rear cover, and a toilet seat pivotally connected to the main body; wherein the toilet seat, after being rotated, covers the toilet base;

the smart toilet further includes a toilet seat temperature control module;

the toilet seat temperature control module is electrically connected to the controller and is used to control temperature of the toilet seat;

the toilet seat temperature control module includes a temperature sensor and a toilet seat heating module;

the temperature sensor and the toilet seat heating module are provided on the toilet seat;

the temperature sensor and the toilet seat heating module are electrically connected to the controller respectively; and the step E further includes performing corresponding operations by the controller based on the input at the key input module: setting the temperature of the toilet seat; and starting the toilet seat temperature control module to adjust the temperature of the toilet seat.

3. The control method of the smart toilet having the function of human blood oxygen detection of claim 1, wherein the step E further includes performing corresponding operations by the controller based on the input at the key input module;

starting, by the controller, the human blood oxygen detection module to conduct the blood oxygen detection;

obtaining, by the human blood oxygen detection module, the electrical signal related to the human blood oxygen saturation value;

transferring the electrical signal to the controller;

after processing, obtaining, by the controller, the human blood oxygen saturation value based on the obtained electrical signal;

controlling, by the controller, the display or voice prompt module or the communication module communicating with the smart device to output the human blood oxygen saturation value.

4. The control method of the smart toilet having the function of human blood oxygen detection of claim 1, wherein the human body sensing module includes an item selected from the group consisting of a capacitive sensor, a pressure sensor, and an inductive electrode plate;

the item selected from the group consisting of a capacitive sensor, a pressure sensor, and an inductive electrode plate is electrically connected to the controller;

the item selected from the group consisting of a capacitive sensor, a pressure sensor, and an inductive electrode plate is used to sense whether the user has sat down; and the item selected from the group consisting of a capacitive sensor, a pressure sensor, and an inductive electrode plate is provided on the toilet base or the machine body.

* * * * *